United States Patent
Cumming et al.

(10) Patent No.: US 12,349,610 B2
(45) Date of Patent: Jul. 1, 2025

(54) APPARATUS AND METHOD FOR BIOMARKER DETECTION

(71) Applicant: THE UNIVERSITY COURT OF THE UNIVERSITY OF GLASGOW, Glasgow (GB)

(72) Inventors: David Robert Sime Cumming, East Dunbartonshire (GB); Valerio Francesco Annese, Glasgow (GB)

(73) Assignee: The University Court of the University of Glasgow, Glasgow (GB)

( * ) Notice: Subject to any disclaimer, the term of this patent is extended or adjusted under 35 U.S.C. 154(b) by 464 days.

(21) Appl. No.: 17/917,965

(22) PCT Filed: Apr. 8, 2021

(86) PCT No.: PCT/EP2021/059158
§ 371 (c)(1),
(2) Date: Oct. 10, 2022

(87) PCT Pub. No.: WO2021/204936
PCT Pub. Date: Oct. 14, 2021

(65) Prior Publication Data
US 2023/0160850 A1 May 25, 2023

(30) Foreign Application Priority Data
Apr. 8, 2020 (GB) .................................... 2005170

(51) Int. Cl.
*G01N 27/414* (2006.01)
*B01L 3/00* (2006.01)

(52) U.S. Cl.
CPC ........ *G01N 27/4148* (2013.01); *B01L 3/5027* (2013.01); *B01L 2300/0663* (2013.01); *B01L 2400/0406* (2013.01)

(58) Field of Classification Search
CPC ........ B01L 2200/0689; B01L 2200/12; B01L 2300/0636; B01L 2300/0663;
(Continued)

(56) References Cited

U.S. PATENT DOCUMENTS

2007/0081920 A1    4/2007   Murphy et al.
2016/0187333 A1*   6/2016   Moll ................. B01L 3/502715
                                                            506/18
(Continued)

FOREIGN PATENT DOCUMENTS

WO    2018/215554 A1   11/2018

OTHER PUBLICATIONS

International Search Report and Written Opinion issued in International Patent Application No. PCT/EP2021/059158 dated Jul. 21, 2021.
(Continued)

*Primary Examiner* — Gurpreet Kaur
(74) *Attorney, Agent, or Firm* — Troutman Pepper Locke LLP

(57) ABSTRACT

A biomarker detection apparatus in which a CMOS-based chip is used to generate independent detection signals from a reaction zone that receives a biological sample, where the biological sample is provided to both a test region and positive and negative control regions within the reaction zone. The independent detection signals can be processed together (i.e. as a group of input parameters for an algorithm) to identify the presence of a biomarker (or a plurality of biomarkers) in a biological sample. The use of sample-specific, independently detectable positive and negative controls facilitates improved detection accuracy.

20 Claims, 4 Drawing Sheets

(58) Field of Classification Search
CPC ....... B01L 2300/126; B01L 2400/0406; B01L 3/5027; G01N 27/4148; G01N 31/228; G01N 33/54373; C12Q 1/001
See application file for complete search history.

(56) References Cited

U.S. PATENT DOCUMENTS

2018/0031548 A1    2/2018  Florescu
2021/0069706 A1*   3/2021  Ünlü ................ B01L 3/502715

OTHER PUBLICATIONS

Hu, C., et al. "Disposable Paper-on-CMOS Platform for Real-Time Simultaneous Detection of Metabolotes" IEEE Transactions on Biomedical Engineering 67(9):2417-2426 (2020), cited in ISR.

Al-Rawhani, M. A., et al. "Multimodal Integrated Sensor Platform for Rapid Biomarker Detection" IEEE Transactions on Biomedical Engineering 67(2):614-623 (2020), cited in ISR.

Al-Rawhani. M. A., et al. "A Colorimetric CMOS-Based Platform for Rapid Total Serum Cholesterol Quantification" IEEE Sensors Journal 17(2):240-247 (2017), cited in ISR.

Annese, V. F., et al. "A monolithic single-chip point-of-care platform for metabolomic prostate cancer detection" Microsystems & Nanoengineering 7(21):1-15 (2021), cited in ISR.

Annese, V. F., et al. "The Multicorder: A Handheld Multimodal Metaolomics-on-CMOS Sensing Platform" IEEE 8th Inernational Workshop on Advances in Sensors and Interfaces pp. 130-135 (7 pages submitted) (2019).

\* cited by examiner

Parameters: W1 = 0/37; W2=0.4; W3=0.23; threshold = 0.9355

APPARATUS AND METHOD FOR BIOMARKER DETECTION

CROSS REFERENCE TO RELATED APPLICATIONS

The present application is a U.S. National Phase Application under 35 U.S.C. § 371 of International Patent Application No. PCT/EP2021/059158 filed Apr. 8, 2021, which claims priority of GB Patent Application No. 2005170.2 filed Apr. 8, 2020. The entire contents of which are hereby incorporated by reference.

FIELD OF THE INVENTION

The present invention relates to an apparatus and method for detecting a biomarker in a biological sample.

BACKGROUND

Metabolomics relates to the study of the metabolome, i.e. the collection of small molecules (<1500 Da) known as metabolites produced by human cells in life [1, 2]. More than 114,000 metabolites have been quantified and/or detected in human fluids, tissues or organs in different concentrations. Specifically, more than 4200 metabolites have been identified in human serum. Due to the vast diversity of chemical structures, there is no single technology available to analyse the entire metabolome.

Metabolism is a vital cellular process, and its malfunction can be a major contributor to many diseases. Metabolites (i.e. substances involved in metabolism) can be good indicators of disease phenotype, and can serve as a metabolic disease biomarkers [3]. Therefore quantification and analysis of metabolites can play a significant role in the study and early diagnosis (detection) of many diseases. Metabolite biomarkers of different diseases are also becoming increasingly well understood which paves the way for developing new diagnostic systems. The importance of the link between metabolomics and a person's state of health is governing the need to look at both targeted and untargeted metabolites. A single metabolite can be a biomarker for several different diseases. In addition, multiple metabolites together can serve as a biomarker for a particular disease.

A commonly used technique for detecting and quantifying metabolites is mass spectrometry (MS). This involves ionising a chemical species and sorting the product ions based on their mass-to-charge ratios. Separation methods such as gas chromatography and liquid chromatography are often required prior to performing a mass spectrometry measurement. Nuclear magnetic resonance (NMR) spectroscopy is another technique which is used for metabolite studies. NMR can be used to detect, identify and quantify a wide range of metabolites without having to first separate them. However, both of these techniques require bulky and expensive equipment, which confines their use to hospitals and laboratories.

As an example, elevated cholesterol levels are well known for their association with an increased risk of coronary heart disease (angina or heart attack), narrowing of the arteries (atherosclerosis), stroke, peripheral heart disease and hypertension. Such conditions are often correlated with poor diet, an excessive fat intake, lack of exercise and other lifestyle choices. Measuring or therapeutic monitoring of cholesterol level in blood serum helps to assess susceptibility of the person to develop coronary artery diseases and hence is a good indicator of the state of health of a person.

One of the diagnostic methods for quantifying cholesterol concentration depends on enzyme-based assays that require a spectrophotometer to measure changes in intensity of colour products from those enzyme reactions. A general purpose spectrophotometer would incorporate a sophisticated setup of a white light source, a monochromator containing a diffraction grating and a light transducer that converts light into electrical signal such as a charge-coupled device (CCD), a photodiode or a photomultiplier tube. The wide spectrum range of the spectrophotometer makes it bulky and power hungry which consequently confines its usefulness to laboratories and hospitals. Another method involves metabolites undergoing chemiluminescence reaction. This method requires a more specialised light detector such as a charge-coupled detector (CCD) to detect low light emission of luminol that is used for quantification of small analyte concentration.

More recently, use of a photodiode in a disposable sensing platform to measure change in colour of enzyme assay has been demonstrated as a means of detecting cholesterol by measuring intensity of transmitted light through assay solution [4]. The platform was based on a complementary metal oxide semiconductor (CMOS)-based photodiode array and a light emitting diode (LED). The photodiode array is fabricated using commercial standard CMOS process, which is readily available for low-cost mass-production.

Photodiodes made in a CMOS process are generally sensitive to light in the 200 nm to 1100 nm range, owing to the bandgap of silicon (1.12 eV). This range makes them suitable for colorimetric enzyme assays that use visible light or fluorescent mediators, which often use wavelengths in the range 400 nm to 700 nm. A colour change within this range can be exploited for a range of enzyme assays, e.g. cholesterol ester hydrolase, cholesterol dehydrogenase, cholesterol esterase and cholesterol oxidase can be exploited to measure metabolites such as cholesterol. For metabolites with low concentrations, more sensitive CMOS compatible detector such as single photon avalanche diode (SPAD) can be integrated on the same chip and therefore, increase the dynamic detection range.

In other recent works, another type of CMOS-based chip fabricated with an integrated ion-sensitive field effect transistor (ISFET) array was used to measure glucose concentration in blood through the activity of hexokinase. The action of the hexokinase on the glucose releases hydrogen ions that are detected by the ISFET [5].

Point-of-care diagnostics are transforming the healthcare industry, by facilitating the use of home-testing to provide an early indication of potential illness and disease. The development of low-cost, rapid, specific and high sensitivity consumable biosensors are at the forefront of the research for user-orientated testing, driven in part by the need for rapid diagnosis and monitoring without overburdening the resources of the healthcare services. For example, glucose biosensors have become widespread in their use for managing diabetes. However, point-of-care devices still remain less accurate and reliable than their more expensive counterparts mentioned above, such as mass spectrometry or nuclear magnetic resonance.

SUMMARY

At its most general, the present invention provides a biomarker detection apparatus in which a CMOS-based chip is used to generate independent detection signals from a reaction zone that receives a biological sample, where the biological sample is provided to both a test region and positive and negative control regions within the reaction zone. The independent detection signals can be processed together (i.e. as a group of input parameters for an algorithm) to identify the presence of a biomarker (or a plurality of biomarkers) in a biological sample. The use of sample-specific, independently detectable positive and negative controls facilitates improved detection accuracy.

The detection apparatus may find particular use in a system for point-of-care detection and quantification of biomarkers (e.g. metabolites) in a biological sample.

In the detection apparatus, the reaction zone may be configured to perform the following on the biological sample:
- a first test that is sensitive to the biomarker,
- a positive control test where a known (pre-loaded) amount of the biomarker is used in addition to the biological sample, and
- a negative control test which is not sensitive to the biomarker.

By taking into account the results of these three separate tests, it is possible to accurately detect and estimate an amount of the biomarker in the sample. In particular, the combination of these three tests may improve an accuracy with which the amount of the biomarker in the sample can be estimated. Moreover, by performing the different tests on the same sample and with the same system (i.e. with the same CMOS chip), a reliability of the biomarker detection/quantification may be improved, by taking into account effects that are specific to that sample and system.

As the positive control test involves a known amount of the biomarker, the positive control test may serve to calibrate a sensitivity of the CMOS-based chip to the biomarker in the sample. This may enable on-the-spot, real-time calibration of the system, which may ensure accurate biomarker detection/quantification using the CMOS-based chip.

The negative control test may enable the system to compensate for effects detected by the CMOS-based chip which are not related to the biomarker. So, for example, the negative control test may serve to compensate for changes in measurement conditions (e.g. sample-to-sample variations, chip-to-chip variations, changes in environmental/measurement conditions, activity loss of reagents, external noise, transient microfluidic effects, etc.). Thus, use of both the positive and negative control tests may improve reliability of the detection/quantification of the biomarker across different systems, samples, and measurement conditions, by enabling effects that could interfere with detection results to be minimised.

According to a first aspect of the invention, there is provided a detection apparatus for detecting a biomarker in a biological sample, the detection apparatus comprising: a sample receiving module arranged to receive the biological sample in a reaction zone, the reaction zone comprising: a test region that is sensitive to presence of the biomarker in the biological sample; a positive control region that is sensitive to presence of the biomarker in the biological sample, and which includes a pre-loaded portion of the biomarker; and a negative control region that is not sensitive to presence of the biomarker in the biological sample; and a CMOS-based sensor unit configured to: independently detect a property of each of the test region, the positive control region, and the negative control region, and output a respective detection signal for each of the test region, the positive control region, and the negative control region, wherein the CMOS-based sensor unit is communicable with an analysis module that is configured to determine information related to a presence of the biomarker in the biological sample using the respective detection signals from the test region, the positive control region, and the negative control region.

Herein, a biological sample may refer to a liquid sample comprising biological material. The biological sample may be a sample of bodily fluid which may contain a biomarker of interest. For example, the biological sample may include blood, blood serum, urine, saliva, interstitial fluid, cerebral spinal fluid or any other accessible bodily fluid.

Herein, a biomarker may refer to a chemical or molecule found in the body. The biomarker may be of diagnostic significance, e.g. it may be useful for identifying or diagnosing a health condition in a patient. For example, biomarkers may include metabolites, proteins, DNA molecules, and RNA molecules.

The sample receiving module may comprise a sample receiving area and a transport structure configured to convey the biological sample received at the sample receiving area to the reaction zone. The sample receiving module may thus serve to receive the biological sample, and transport it to the reaction zone. The sample receiving area may include an inlet or the like for receiving the biological sample. The transport structure may include a fluid conducting mechanism for conveying the biological sample to the reaction zone. For example, the fluid conducting mechanism may be configured to transport the biological fluid via capillary action. In some embodiments, the transport structure may comprise a paper strip or other capillary structure for transporting the biological sample to the reaction zone by capillary action.

The reaction zone includes three different regions: the test region, the positive control region, and the negative control region. The test region, the positive control region, and the negative control region may each be spatially separated from one another. This may avoid cross-talk between reactions occurring in the different regions, as well as facilitate independent measurement of the different regions by the CMOS-based sensor unit. In some cases, there may be barriers between the test region, the positive control region, and the negative control region, in order to prevent or inhibit the biological sample from flowing between the regions.

The sample receiving module may be configured to transport the biological sample to each of the regions in the reaction zone. Thus, each of the test region, the positive control region, and the negative control region may receive a respective portion of the biological sample.

The test region is sensitive to the presence of the biomarker in the biological sample. Thus, a property of the test region may change in response to presence of the biomarker in the biological sample. For instance, the change in the property may be related to (e.g. proportional to) a concentration of the biomarker in the biological sample. This property of the test region may be detected by the CMOS-based sensor unit, and used to determine information related to a presence of the biomarker in the biological sample, as discussed further below.

The test region may be configured to support a chemical reaction or chain of reactions involving the biomarker. Thus, the test region may include a test material (e.g. one or more reagents) configured to support a reaction involving the biomarker, when the biological sample is transported to the test region. As an example, the test region may include an enzyme that participates in a reaction (or reaction chain) involving the biomarker. The reaction in the test region involving the biomarker may cause the detected property of the test region to change.

The positive control region is similarly sensitive to presence of the biomarker in the biological sample. Additionally, the positive control region includes a pre-loaded portion of the biomarker disposed therein. A property of the positive control region may change in response to an amount (or concentration) of biomarker in the positive control region when the biological sample is introduced into the positive control region. When the biological sample is introduced into the positive control region (e.g. by the sample receiving module), biomarkers present in the biological sample are combined with the pre-loaded portion of biomarker disposed in the positive control region. As a result, both the biomarkers from the biological sample and from the positive control region may contribute to the change in the property of the positive control region. This property of the positive control region may be detected by the CMOS-based sensor unit, and used to determine information related to a presence of the biomarker in the biological sample, as discussed further below.

Similarly to the test region, the positive control region may be configured to support a chemical reaction or chain of reactions involving the biomarker. The positive control region may include a test material (e.g. one or more reagents) configured to support a reaction involving the biomarker, when the biological sample is transported to the positive control region. The test material may be the same as that which is used in the test region. Both the biomarkers from the biological sample and from the positive control region may participate in the reaction with the test material when the biological sample is introduced to the positive control region.

The pre-loaded portion of the biomarker in the positive control region may include a known concentration (or amount) of the biomarker. The known concentration of biomarker may be selected to ensure that the change in the property of the positive control region is detectable by the CMOS-based sensor unit, regardless of the concentration of the biomarker in the sample. For example, the known concentration may be selected to be above a detection threshold for the CMOS-based sensor unit (i.e. above a concentration level at which the CMOS-based sensor unit can reliably detect presence of the biomarker). The concentration of the pre-loaded portion of the biomarker may, for example, be selected using a known calibration curve of the CMOS-based sensor unit, to ensure that the sample sizes are within a detection range of the CMOS-based sensor unit. In this manner, even when there is no, or only a very low concentration of, biomarker in the biological sample, the CMOS-based sensor unit may still detect a change in the property of the positive control region (due to the pre-loaded portion of biomarker disposed in the positive control region). This may ensure that a meaningful signal can be obtained from the positive control region, which may enable the detection apparatus to be reliably calibrated.

The pre-loaded portion of biomarker may be arranged in the positive control region at a different location compared to the test material. This may avoid reaction of the pre-loaded portion of biomarker prior to introduction of the biological sample into the positive control region. The transport structure may be configured to entrain the pre-loaded portion with the biological sample before it enters the positive control region. That is, the pre-loaded portion is automatically brought into the reaction zone by the conveying action of the transport structure.

The negative control region is not sensitive to presence of the biomarker in the biological sample. Thus, unlike the test region and the positive control region, the negative control region is not configured to support a reaction involving the biomarker. In other words, the test region may not include any reagent configured to react with the biomarker. The negative control region may therefore be used to monitor non-specific activity, i.e. changes produced by the biological sample in the reaction zone which are not related to presence of the biomarker in the sample.

The CMOS-based sensor unit is arranged to independently detect properties of the test region, positive control region and negative control region. The CMOS-based sensor unit is configured to produce one or more detection signals that are indicative of the detected properties of the test region, positive control region and negative control region.

In some embodiments, the reaction zone may include two or more test regions, two or more positive control regions, and/or two or more negative control regions. In this manner, multiple instances of the same measurement may be performed in the reaction zone, which may improve an accuracy of biomarker detection and/or quantification. The test regions, positive control regions and negative control regions may be configured as discussed above. The CMOS-based sensor unit may be configured to independently detect a property of each of the regions, and output a respective detection signal for each of the two or more test regions, two or more positive control regions, and/or two or more negative control regions. Then, for example, the detection signals from a same type of region may be combined (e.g. averaged) to provide a detection signal representative of the detected property for that region type. For instance, the detection signals from the two or more test regions may be combined to provide a detection signal representative of the detected property for the two or more test regions.

The CMOS-based sensor unit may include an array of sensor elements (or sensors) disposed on a substrate and arranged to detect the properties of the different regions. The array of sensor elements may include a first set of sensor elements arranged to detect the property of the test region, a second set of sensor elements arranged to detect the property of the positive control region, and a third set of sensor elements arranged to detect the property of the negative control region. Each sensor element may be independently addressable, in order to obtain signals corresponding to each region in the reaction zone.

Herein the phrase "CMOS-based" may mean that the sensor unit is capable of fabrication using conventional semiconductor chip processes, e.g. comprising a series of depositing, masking and etching steps on a substrate. The sensor unit and its constituent components may thus be semiconductor components. The sensor unit may therefore be in the form of a semiconductor chip. This may enable the sensor unit to be mass-produced at low cost. The detection apparatus may thus be embodied as a compact hand-held device which is easily transportable, thus facilitating rapid point-of-care diagnostics. Compared with current analytical methods for metabolite detection and quantification, no expensive detection equipment may be required.

The properties of the test region, positive control region and negative control region that are detected by the CMOS-based sensor unit may be physical or chemical. For example, the CMOS-based sensor unit may be configured to detect changes in appearance, chemical composition, mass, temperature, etc. of the different regions. The same property may be detected by the CMOS-based sensor unit for each of the regions.

For example, the CMOS-based sensor unit may comprise an array of optical sensors, to detect changes in appearance of the different regions in the reaction zone (e.g. by capturing an image or determining a change in optical properties thereof). The detection apparatus may further comprise an optical source (e.g. LED or the like) for illuminating the reaction zone with optical radiation. In one example, an optical sensor may include a spectral absorption sensor, e.g. a photodiode or an array of photodiodes and/or a single photon avalanche diode (SPAD) to increase the detection dynamic range.

As another example, the CMOS-based sensor unit may comprise an array of chemical sensors, to detect changes in chemical composition of the different regions in the reaction zone. Such a chemical sensor may include a pH sensor, e.g. comprising an ion field effect transistor (ISFET). In such a case, the detection apparatus may further include a reference electrode arranged to apply a voltage to the reaction zone.

In some embodiments, the CMOS-based sensor unit may have multiple sensing modalities, e.g. it may be capable of sensing multiple properties for each of the regions. For example, each sensor element in the array may actually include two or more sensors, each of which is configured to detect a different property of the reaction zone. The detection apparatus may thus be capable of simultaneous detection of multiple biomarkers. This may be particularly useful in cases where detection of multiple biomarkers is needed to classify a biological sample for a certain pathological condition or disease.

The detection apparatus may be provided as a self-contained unit. For example, the detection apparatus may be provided as a cartridge, e.g. having a housing in which the reaction zone and CMOS-based sensor unit are disposed.

The analysis module may be provided as part of the detection apparatus unit. However, it may preferably be located in a separate controller or reader device that is detachably connectable to the detection apparatus.

In another aspect, the invention may provide a system comprising the detection apparatus and the analysis module, e.g. configured as a cartridge and reader respectively.

The analysis module may be configured to receive output signals from the CMOS-based sensor unit indicative of the detected properties of the test region, positive control region and negative region. In this manner, the analysis module may process the output signals received from the CMOS-based sensor unit in order to determine information related to presence of the biomarker in the biological sample.

The analysis module may be configured to control measurements performed by the CMOS-based sensor unit, e.g. by transmitting one or more control signals to the CMOS-based sensor unit.

The analysis module may include any suitable processing device capable of receiving and processing the output signals from the CMOS-based sensor unit, and of controlling the CMOS-based sensor unit. The analysis module may include a memory for storing data received from the CMOS-based sensor unit.

In some embodiments, the analysis module may be implemented by a dedicated microprocessor which is configured to provide control signals to, and receive output signals from, the CMOS-based sensor unit. Such a dedicated microprocessor may, for example, be mounted on a printed circuit board (PCB) together with the CMOS-based sensor unit. Alternatively, the analysis module may be implemented by a separate device (e.g. a reader device), which is connectable to communicate with the CMOS-based sensor unit. In some cases, the analysis module may be implemented by a computing device (e.g. laptop or tablet computer) or smartphone having suitable software installed thereon.

The CMOS-based sensor unit may include a communication interface for connecting the analysis module to the CMOS-based sensor unit.

The analysis module may employ any suitable algorithm for determining the information related to a presence of the biomarker in the biological sample, based on the detected properties of the different region. As discussed above, by taking into account the properties of the different regions in the determination, it is possible to minimise or compensate for effects that could interfere with accurate detection/quantification of the biomarker in the biological sample. In particular, the detected properties for the positive control region and the negative control region may be used to calibrate and/or correct the measurement of the test region.

Herein, information related to a presence of the biomarker in the biological sample may refer to a concentration or amount of the biomarker in the biological sample. Such information may also simply refer to a positive or negative detection result (i.e. an indication of whether the biomarker is present in the biological sample or not).

The CMOS-based sensor unit may be configured to simultaneously detect the properties of the test region, positive control region and negative control region. In this manner, the properties of the positive and negative control regions may be detected at the same time as the property of the test region. This may serve to ensure that the properties of the different regions are obtained under the same experimental conditions. As a result, accuracy of the determination result may be improved. Simultaneous detection may, for example, be implemented by obtaining readings from the sensor elements in the array substantially simultaneously. Then, the output signals provided by the CMOS-based sensor unit may be indicative of the properties of the different regions at corresponding points in time.

In some embodiments, the positive control region may include a first positive control region and a second positive control region, the first positive control region including a first pre-loaded portion of the biomarker and the second control region including a second pre-loaded portion of the biomarker, the second pre-loaded portion including a larger amount of the biomarker than the first pre-loaded portion; and the detected property of the positive control region may include independently detected properties of the first positive control region and the second positive control region. In other words, the CMOS-based sensor unit may be configured to separately detect properties of the first positive control region and the second positive control region. Providing two positive control regions with different pre-loaded amounts of the biomarker may improve the accuracy with which the detection apparatus can be calibrated. Indeed, the two positive control regions effectively provide two data points which the analysis module can use to calibrate a sensitivity of the CMOS-based sensor unit to the biomarker. Of course, more than two positive control regions may be used (e.g. each with a different size sample), to further improve accuracy of the measurement.

The second pre-loaded portion may have a greater concentration of biomarker than the first pre-loaded portion. The sample sizes (or concentrations) of the first and second pre-loaded portions may be selected using a known calibration curve of the CMOS-based sensor unit, to ensure that the sizes (or concentrations) are within a detection range of the CMOS-based sensor unit. Additionally, the sizes (or concentrations) of the first and second pre-loaded portions may be selected such that they are within a linear response region of the CMOS-based sensor unit, e.g. so that they result in an output signal that is proportional to the biomarker concentration.

Each of the first positive control region and the second positive control region may be sensitive to presence of the biomarker in the biological sample, as discussed above. Thus, the properties of the first and second positive control regions may change in response to introduction of the biological sample, as discussed above.

The analysis module may be configured to: determine information indicative of a reaction rate of a reaction in the test region involving the biomarker, based on the detected property of the test region and the detected property of the negative control region; and determine the information related to the presence of the biomarker in the biological sample based at least in part on the information indicative of the reaction rate. As discussed above, when the biological sample is introduced to the test region, a reaction involving the biomarker may take place in the test region, resulting in a change of the detected property of the test region. The rate change of the reaction (and thus of the detected property) may be related (e.g. proportional) to the initial concentration of biomarker in the biological sample.

As the negative control region is not sensitive to the biomarker, any changes in the detected property of the negative control region may be unrelated to presence of the biomarker in the biological sample, and may result from reactions involving other components of the biological sample. So, by taking into account the detected property of the negative control region, it is possible to determine changes in the detected property of the test region that are solely due to reaction of the biomarker in the test region. This may enable accurate determination of the reaction rate in the test region, thus enabling accurate detection/quantification of the biomarker in the biological sample.

As an example, an initial reaction rate $r_t$ for the test region may be determined based on a rate of change of the detected property of the test region. The reaction rate $r_t$ may be indicative of reactions occurring in the test region that involve both the biomarker and other components of the biological sample. An initial reaction rate $r_n$ for the negative control region may be determined based on a rate of change of the detected property of the negative control region. The reaction rate $r_n$ may be indicative of reactions occurring in the negative control region (and the rest of the reaction zone) involving components of the biological sample other than the biomarker. Then, the reaction rate $r_t$ of the reaction in the test region involving the biomarker may be determined as:

$$r_t^* = r_t - r_n \qquad (1)$$

Thus, the reaction rate $r_t^*$ is corrected for effects that are unrelated to presence of the biomarker in the biological sample. As a result, $r_t^*$ may be used to improve an accuracy with which the biomarker can be detected and/or quantified in the biological sample.

The analysis module may be configured to: determine information indicative of a measurement sensitivity, based on the detected property of the positive control region and a size of the sample of the biomarker in the positive control region; and determine the information related to the presence of the biomarker in the biological sample based at least in part on the information indicative of the measurement sensitivity. The measurement sensitivity may, for example, serve relate a reaction rate of a reaction in the test region involving the biomarker to a concentration (or amount) of the biomarker in the biological sample. In this manner, once the reaction rate for the biomarker in the test region has been determined (e.g. as discussed above), the measurement sensitivity may be used to determine a concentration of the biomarker in the biological sample.

As an example, the measurement sensitivity S may be determined as:

$$S = \frac{r_a - r_t^*}{A} \qquad (2)$$

where $r_a$ corresponds to a reaction rate for the positive control region (e.g. determined based on a rate of change of the detected property of the positive control region), and A corresponds to a concentration of the sample of the biomarker in the positive control region.

As another example, where the positive control region includes a first positive control region and a second positive control region, the measurement activity S may be determined as:

$$S = \frac{r_b - r_a}{B - A} \qquad (3)$$

where $r_a$ corresponds to a reaction rate for the first positive control region (e.g. determined based on a rate of change of the detected property of the first positive control region), where $r_b$ corresponds to a reaction rate for the second positive control region (e.g. determined based on a rate of change of the detected property of the first positive control region), A corresponds to a concentration of the first sample of the biomarker in the first positive control region, and B corresponds to a concentration of the second sample of the biomarker in the second positive control region. The concentration B may be greater than concentration A. The inventors have found that using equation (3) for determining the measurement sensitivity may lead to improved accuracy (e.g. compared to equation (2)), as it does not rely on the measurement in the test region. Thus, using two separate positive control regions may lead to an improved accuracy of the measurement.

The analysis module may be configured to determine the information related to a presence of the biomarker in the biological sample based on the information indicative of a reaction rate and the information indicative of a measurement sensitivity. In this manner, the measurements performed on the different regions of the reaction zone are taken into account in the determination.

For example, the analysis module may be configured to determine a concentration T of the biomarker in the biological sample using the following equation:

$$T = \frac{r_t^*}{S} \qquad (4)$$

The reaction rate $r_t^*$ may be determined using equation (1) above, whilst the measurement sensitivity S may be determined using equation (2) or (3) above, depending on configuration of the reaction zone. Alternatively, the concentration T may be determined using the Michaelis-Menten model.

The test region may include a set of reagents configured to cause a change in the detected property of the test region in response to a biological sample comprising the biomarker coming into contact with the test region.

The set of reagents may include a reagent that is specific to the biomarker. The reagent that is specific to the biomarker may react directly with the biomarker, or participate in a reaction involving the biomarker. For example, the reagent that is specific to the biomarker may include an enzyme that reacts with the biomarker. The other reagents in the set of reagents may serve to produce a change to the detected property of the test region in response to the reaction between the biomarker and the reagent that is specific to the biomarker.

As an example, where the detected property of the test region is a change in colour of the test region (i.e. a colorimetric measurement), the set of reagents may include a first enzyme that is specific to the biomarker which reacts with the biomarker to produce hydrogen peroxide. The set of reagents may further include a second enzyme (e.g. peroxidase) and colour-changing reagents such as o-dianisidine or phenol/4-antipyrine. The second enzyme can then catalyse a reaction between hydrogen peroxide and the colour-changing reagents, thus resulting in a change of colour of the test region which is detectable by the CMOS-based sensor unit.

The negative control region may include the set of reagents, except for the reagent that is specific to the biomarker. Thus, as the reagent that is specific to the biomarker is omitted from the negative control region, the negative control region is not sensitive to the biomarker. However, as the other reagents from the set of reagents are present in the negative control region, the negative control region may be used to determine the effect of these other reagents on the detected properties. So, in the example above, the negative control region may include the second enzyme and the colour-changing reagents, but not the first enzyme.

The positive control region may include the set of reagents, i.e. the same set of reagents used in the test region. Where the positive control region includes first and second positive control regions, both control regions may include the set of reagents. In this manner, the same set of reactions may be carried out in the positive control region as in the test region, thus enabling effective calibration of the measurement of the test region.

The sample of the biomarker and the set of reagents may be arranged in the positive control region such that a biological sample transported to the positive control region by the sample receiving module comes into contact with the pre-loaded portion of biomarker before it comes into contact with the set of reagents. This may avoid the pre-loaded portion of biomarker interacting with the reagents in the positive control region prior to introduction of the biological sample. For example, the pre-loaded portion of biomarker may be placed "upstream" of the set of reagents, e.g. the pre-loaded portion of biomarker may be closer to an inlet of the positive control region than the set of reagents. Then, when the biological sample is introduced to the positive control region, it may first encounter the pre-loaded portion of biomarker, at least some of which may then be transported with the biological sample to the set of reagents. In embodiments where there are first and second positive control regions, the first and second pre-loaded portions of the biomarker may similarly be arranged upstream of the respective set of reagents.

The relevant reagents may be loaded into the regions of the reaction zone using any suitable techniques. Suitable techniques include immobilisation, entrapment, encapsulation techniques and printing (e.g. ink-jet printing) techniques. The sample of the biomarker may be loaded into the positive control region using similar techniques. Loading the reagents and biomarker sample in this manner may ensure that the reagents and biomarker sample are immobilised within the reaction zone, so that reactions do not occur prior to introduction of the biological sample.

In some embodiments, the set of reagents may be freeze-dried. In other words, the set of reagents in one or more of the regions may be in a dehydrated (e.g. dry) state. This may facilitate storing and transport of the detection apparatus. Then, when the biological sample is introduced to the detection apparatus, the biological sample may re-hydrate the reagents, thus enabling reactions to take place in the reaction zone.

In some embodiments, each of the test region, positive control region and negative control region may be provided within a respective microfluidic channel or well. In this manner, each region of the reaction zone may be spatially confined to its respective microfluidic channel or well. A microfluidic channel may be configured to receive the biological sample from the sample receiving module, and transport a portion of the biological sample along its length via capillary action. Similarly, a microfluidic well may be configured to receive and contain a portion of the biological sample from the sample receiving module.

The respective microfluidic channels or wells may be defined by a microstructure which is disposed on the CMOS-based sensor unit. Thus, the test region, positive control region and negative control region may be disposed on a surface of the CMOS-based sensor unit. The microstructure may be arranged on the CMOS-based sensor unit such that the test region, positive control region and negative control region are aligned with respective sets of sensor elements of the CMOS-based sensor units. The microstructure may be made of any suitable material, such as an epoxy resin. The microstructure may be fabricated using known techniques, such as lithography, injection moulding, 3D printing or other suitable technique.

However, the test region, positive control region and negative control region may be defined in other ways, and need not necessarily be provided directly on the CMOS-based sensor unit. For example, in some embodiments, the regions of the reaction zone may be formed in or on a paper strip that is disposed over the CMOS-based sensor unit. The paper strip may, for example, be a part of the sample receiving module that extends of the CMOS-based sensor unit.

The respective microfluidic channels or wells may be covered by a lid. This may serve to entrap the reagents and biomarker sample in their respective regions. This may facilitate storage and transport of the detection apparatus, as well as protect the reagents and biomarker sample from the environment. The lid may be a part of the microstructure, e.g. it may be bonded to the microstructure or formed integrally as part of the microstructure. To further protect the reagents and biomarker sample from the environment, the reaction zone may be placed in a vacuum-sealed enclosure. The vacuum-sealed enclosure may then be opened when the detection apparatus is to be used.

The analysis module may be provided as part of the detection apparatus, e.g. it may be integrated with the detection apparatus. Alternatively, the analysis module may be provided as a separate component to the detection apparatus, e.g. it may be connectable to the to the detection apparatus in order to communicate with the CMOS-based sensor unit.

Thus, in some embodiments, the analysis module may be removably connectable to the detection apparatus. The analysis module may be connectable to the cartridge via a communication interface configured to communicatively couple the analysis module to the CMOS-based sensor unit. The communication interface may be any suitable wired or wireless communication interface, for communicating signals between the analysis module and the CMOS-based sensor unit. The detection apparatus may be configured as a single-use product, e.g. it may be disposable or recyclable. By making the analysis module removably connectable to the detection apparatus, it need not be disposed of with the detection apparatus after use (e.g. it can be disconnected from the apparatus after use), and so can be used with multiple different detection apparatuses across different measurements.

The detection apparatus may be provided as a cartridge that is connectable to the analysis module. In other words, the reaction zone and CMOS-based sensor unit may be provided as an integrated device which is connectable to the analysis module. As an example, the cartridge may include a housing in which the CMOS-based sensor unit and reaction zone are disposed. The sample receiving module may also be included in the cartridge. Alternatively, where the sample receiving module is not included in the cartridge, the cartridge may include a receiving portion for receiving the sample receiving module.

The analysis module may be in the form of a reader device that is configured to communicate with the detection apparatus.

The analysis module may further be configured to communicate with a separate computing device (e.g. laptop, tablet computer or smartphone), e.g. to transmit data collected from the CMOS-based sensor unit to the computing device. The computing device may then store and/or analyse the collected data.

In some embodiments, the analysis module (or a separate computing device to which it is connected) may be further configured to classify the biological sample based on the information related to a presence of the biomarker in the biological sample. For example, the analysis module may be configured to classify the sample as "healthy" or "non-healthy", depending on the presence and/or amount of the biomarker in the sample. In some cases, the analysis module may be configured to classify the sample as indicative of a particular health condition, e.g. depending on the presence and/or amount of the biomarker in the sample. The analysis module may include a model for classifying the biological sample based on the information related to a presence of the biomarker in the biological sample. Any suitable type of classification model for classifying samples based on the presence of a biomarker in the sample may be used. As an example, the model may include a machine learning model that is trained to classify the biological sample.

In some cases, such classification of the biological sample may be performed by the analysis module. In other cases, such classification may be performed by a separate computing device, e.g. based on data received from the analysis module.

According to another aspect of the invention, there is provided a method of detecting a biomarker in a biological sample, the method comprising: introducing the biological sample into a reaction zone, the reaction zone comprising: a test region that is sensitive to presence of the biomarker in the biological sample, a positive control region that is sensitive to presence of the biomarker in the biological sample, and that includes a pre-loaded portion of the biomarker, and a negative control region that is not sensitive to presence of the biomarker in the biological sample; independently detecting, using a CMOS-based sensor unit, a property of each of the test region, the positive control region, and the negative control region; outputting a respective detection signal for each of the test region, the positive control region, and the negative control region; and determining, using the respective detection signals from the test region, positive control region and negative control region, information related to presence of the biomarker in the biological sample.

The method may be implemented with the detection apparatus discussed above. Accordingly, any features discussed above in relation to the first aspect of the invention may be apply to the method.

The method may comprise simultaneously detecting the properties of the test region, positive control region and negative control region.

In some embodiments, determining the information related to a presence of the biomarker in the biological sample may include determining information indicative of a reaction rate of a reaction in the test region involving the biomarker, based on the detected property of the test region and the detected property of the negative control region.

In some embodiments, determining the information related to a presence of the biomarker in the biological sample may include determining information indicative of a measurement sensitivity, based on the detected property of the positive control region and a size of a preloaded portion of biomarker in the positive control region.

In some embodiments, the information related to a presence of the biomarker in the biological sample may be determined based on the information indicative of a reaction rate and the information indicative of a measurement sensitivity.

In some embodiments, the method may further comprise classifying the biological sample based on the information related to a presence of the biomarker in the biological sample.

BRIEF DESCRIPTION OF THE DRAWINGS

Embodiments of the invention will now be described by way of example with reference to the accompanying drawings, in which.

DETAILED DESCRIPTION

Figure 1:
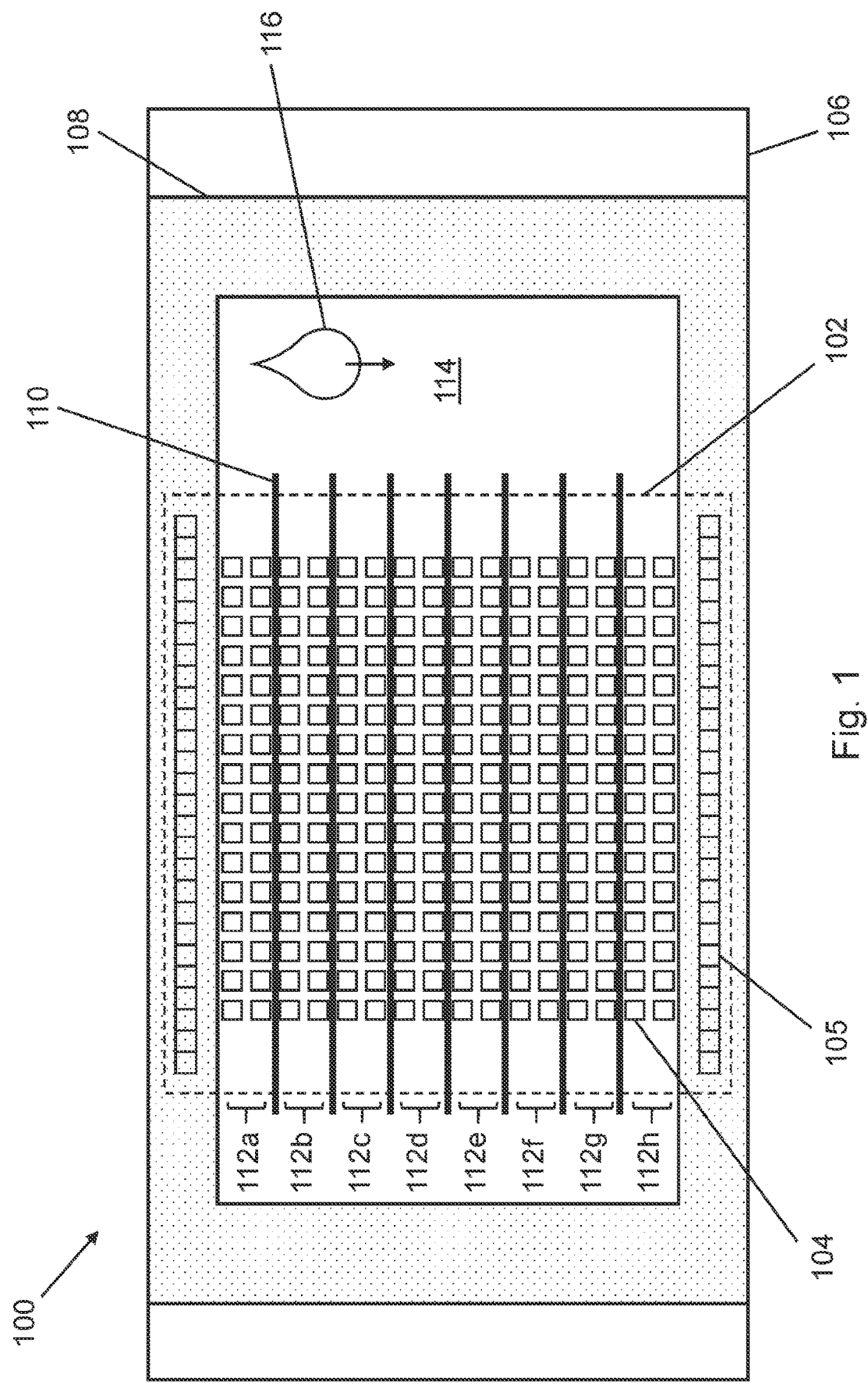
FIG. 1 shows a schematic plan view of a detection apparatus according to an embodiment of the invention.

FIG. 1 shows a schematic plan view of a detection apparatus 100 that may be part of a system according to the invention for detecting a biomarker in a biological sample.

The detection apparatus 100 includes a CMOS-based sensor unit 102, which includes an array of sensor elements 104 disposed at a surface of the sensor unit 102. In the example shown, the sensor unit 102 has a 16×16 array of sensor elements 104, however other sizes of array may be used in other examples. The sensor unit 102 may be in the form of a semiconductor chip which is fabricated using conventional semiconductor chip processes. The sensor unit 102 may typically be in the form of a silicon integrated circuit (IC). The sensor elements 104 may be photosensitive (e.g. photodiodes or/and single photon avalanche diodes (SPADs)) or chemical sensors (e.g. ion-sensitive field-effect transistors (ISFETs) or electrochemical electrodes) as will be discussed in further detail below. In some cases, each sensor element 104 may itself include multiple sensors, each of which can detect a different physical or chemical property.

Each of the sensor elements 104 in the array is individually addressable, such that a respective output signal can be obtained from each sensor element 104. In particular, as discussed in more detail below, a controller of the system may be communicatively coupled to the sensor unit 102, in order to control measurements performed by the array of sensor elements 104, and to obtain output signals from the array. The sensor unit 102 includes a series of bonding pads 105 disposed along edges of the sensor unit. The bonding pads 105 are electrically connected to the sensor elements 104, such that each sensor element in the array can be individually addressed via the bonding pads 105.

The sensor unit 102 is disposed on a backing substrate 106, and an outline of the sensor unit 102 is shown by the dashed lines in FIG. 1. The substrate 106 may include a printed circuit board (PCB) to which the bonding pads 105 are electrically connected. The apparatus 100 may further include an electrical connector (not shown) which is electrically connected to the bonding pads 105 via the PCB. In this manner, a controller may be electrically connected to the sensor unit 102 via the connector of the apparatus 100, such that the controller can perform measurements with the array of sensor elements 104. In some cases, the PCB may include a microcontroller which is configured to address each of the sensor elements 104 in the array. Alternatively, such an addressing function may be performed by the controller which is connected to the apparatus 100. In some cases, the substrate 106 may be in the form of a chip carrier to which the sensor unit 102 is bonded, such as a ceramic chip carrier.

A microstructure is disposed on the sensor unit 102 and substrate 106, in order to define a sample receiving area and reaction zone. The microstructure includes an outer ring (or barrier) 108 disposed on the sensor unit 102 and substrate 106, and which encloses (i.e. is disposed around) an area including the array of sensor elements 104 on the sensor unit 102. The area enclosed by outer ring 108 also includes a portion of the substrate 106 adjacent to the sensor unit 102. The bonding pads 105 of the sensor unit 102 are embedded in the outer ring 108, which may serve to protect electrical connections formed at the bonding pads 105. The microstructure further includes a set of barriers 110 formed on a surface of the sensor unit 102. The microstructure may, for example, be made of an epoxy resin, and a process for forming the microstructure is discussed in more detail below in relation to FIG. 2.

The barriers 110 are arranged to define a series of linear microfluidic channels 112a-h on the surface of the sensor unit 102. In particular, the barriers 110 are arranged such that the microfluidic channels 112a-h extend across the array of sensor elements 104. The microfluidic channels 112a-h are defined in relation to the array of sensor elements 104 such that a respective subset of the sensor elements 104 is disposed within each microfluidic channel. In this manner, the sensor elements 104 in each microfluidic channel can detect a property of a fluid (e.g. biological sample) in that channel. In the example shown, the barriers 110 are arranged such that two rows of sensor elements 104 from the array are disposed within each microfluidic channel (i.e. a total of 32 sensor elements per channel). However, in other examples, different configurations of microfluidic channels may be used. Together, the microfluidic channels 112a-h on the sensor unit 102 serve to define a reaction zone of the apparatus 100, with the microfluidic channels 112a-h corresponding to different regions of the reaction zone.

A sample receiving area 114 is arranged on the substrate 106 adjacent to the sensor unit 102, and defined in part by the outer ring 108. The sample receiving area 114 is arranged to receive a biological sample (e.g. as illustrated by reference numeral 116 in FIG. 1), and to distribute the biological sample amongst the microfluidic channels 112a-h on the sensor unit 102. The biological sample may be a liquid sample, such as a bodily fluid. Thus, a biological sample deposited in the sample receiving area 114 may flow towards an inlet side of the microfluidic channels 112a-h, such that a respective portion of the biological sample enters and flows along each microfluidic channel. The microfluidic channels 112a-h may be dimensioned to cause a fluid sample to flow along the channels under capillary action. The sample receiving area 114 may be in the form of a reservoir or receptacle that is defined on the inlet side of the microfluidic channels 112a-h by the outer ring 108. In some cases, the sample receiving area 114 may include a capillary structure (not shown) for receiving and transporting the biological sample to the microfluidic channels 112a-h via capillary action. This may facilitate distributing the biological sample amongst the microfluidic channels 112a-h. For example, paper may be used in the sample receiving area 114 to receive the biological sample and transport it to the microfluidic channels 112a-h. The sample receiving area 114 may also be referred to as a sample receiving module.

As mentioned above, the microfluidic channels 112a-h constitute a reaction zone of the apparatus 100, and serve to define different regions of the reaction zone. The microfluidic channels 112a-h are split up into sets of channels corresponding to test regions, positive control regions, and negative control regions, respectively. In the example shown, channels 112d and 112e correspond to test regions, channels 112c and 112f correspond to first positive control regions, channels 112b and 112g correspond to second positive control regions, and channels 112a and 112h correspond to negative control regions. Of course, if different embodiments, different arrangements of the channels and regions may be used.

Channels 112d and 112e, which correspond to the test regions, are configured to be sensitive to a biomarker of interest (i.e. a biomarker that is to be detected within the biological sample). In particular, the channels 112d and 112e are configured to support a reaction or chain of reactions involving the biomarker when the biological sample is introduced into the channels 112d and 112e. Furthermore, the reaction supported by the channels 112d and 112e is configured to produce a change in a property that is detectable by the sensor elements 104 located in those channels. This is achieved by placing a set of reagents in the channels 112d and 112e, the set of reagents including a reagent that is specific to the biomarker, i.e. which is configured to directly interact/react with the biomarker. For example, the reagent that is specific to the biomarker may include an enzyme that is known to react with the biomarker. The set of reagents may further include reagents that are configured to produce a change in the detected property in response to the reaction between the biomarker and the specific reagent. In this manner, when the biological sample is introduced into the channels 112d and 112e, reactions involving the biomarker in the sample may take place, thus causing a change in the property detected by the sensor elements 104 in those channels. The change in the detected property may be related to concentration of the biomarker in the sample, thus enabling detection/quantification of the biomarker in the sample.

Channels 112c and 112f (which correspond to the first positive control regions) and channels 112b and 112g (which correspond to the second positive control regions) are also configured to be sensitive to the biomarker. So, each of channels 112c, 112f, 112b, 112g is provided with the same set of reagents that is used in the test regions. Additionally, these channels each include a respective sample of the biomarker. The biomarker samples in channels 112b and 112g have a larger amount (and concentration) of biomarker compared with the samples located in the channels 112c and 112f. The biomarker samples in channels 112c, 112f, 112b, 112g are located such that when the biological sample is introduced into these channels, the biological sample encounters the biomarker samples before it encounters the set of reagents. Thus, the biomarker samples in channels 112c, 112f, 112b, 112g may be located closer to the sample receiving area 114 than the sets of reagents in those channels.

When a biological sample is introduced into the channels 112c, 112f, 112b, 112g, the biological sample may entrain the biomarker samples along the channels until it reaches the sets of reagents. Thus, the biomarker samples provided in the channels 112c, 112f, 112b, 112g may participate in the reactions in these channels when a biological sample is introduced. Similarly to the discussion in relation to the test regions, the sensor elements 104 located in channels 112c, 112f, 112b, 112g are configured to detect changes in properties that result from the reactions in those channels. The amount of biomarker in each of the biomarker samples in channels 112c, 112f, 112b, 112g is known, and selected such that a response is detectable by the relevant sensor elements 104, regardless of the actual concentration of biomarker in the biological sample. This may ensure that a change in the detected property is detectable by the sensor elements 104 in the channels 112c, 112f, 112b, 112g, even when there is no or very little biomarker in the biological sample. For example, the amount of biomarker in each of the biomarker samples may be selected based on a known calibration curve for the sensor elements 104 of the sensor unit 102. The amount of biomarker in the biomarker samples may be selected such that they result in a signal that lies in a linear response region of the sensor elements 104.

Channels 112a and 112h, which correspond to the negative control regions, are not configured to be sensitive to the biomarker. The channels 112a and 112h include the set of reagents used in the other channels, except that the reagent that is specific to the biomarker is omitted. The sensor elements 104 in the channels 112a and 112h are arranged to detect changes in a property of these channels when a biological sample is introduced therein. As the reagents included in the channels 112a and 112h do not include the reagent that is specific to the biomarker, any changes in the detected parameter may be a result of reactions involving components other than the biomarker in the biological sample.

As an example, the detection apparatus 100 may be used to perform colorimetric measurements on a biological sample. In such a case, the sensor elements 104 may be in the form of photodiodes. Thus, the sensor elements 104 may detect changes in appearance (e.g. colour, absorbance) of a sample located in the different channels 112a-h. The detection apparatus 100 may further include a light source (e.g. LED) arranged to illuminate the reaction zone on the sensor unit 102. For such a colorimetric measurement, the set of reagents may include a first enzyme that is specific to the biomarker which reacts with the biomarker to produce hydrogen peroxide. The set of reagents may further include a second enzyme (e.g. peroxidase) and colour-changing reagents such as o-dianisidine or phenol/4-antipyrine. The second enzyme can then catalyse a reaction between hydrogen peroxide and the colour-changing reagents, thus resulting in a change of colour of the test region which is detectable by the sensor elements 104. The first enzyme may be omitted from the negative test regions, so that they are not sensitive to the biomarker. An example of a colorimetric measurement for detecting cholesterol in a sample is described in [4], where cholesterol oxidase is used as the first enzyme.

As another example, the detection apparatus 100 may be used to perform chemiluminescence measurements on a biological sample. For such a measurement, the sensor elements 104 may be in the form of single photon avalanche diodes (SPADs). The SPADs may be used to detect light that is emitted during reactions that occur in the channels 112a-h following introduction of a biological sample. The set of reagents may include a first enzyme that reacts with the biomarker to produce hydrogen peroxide, together with Luminol ($C_8H_7N_3O_2$) and a second enzyme (e.g. peroxidase). The second enzyme may catalyse a reaction between the hydrogen peroxide and Luminol, which emits a number of photons that can be detected by the SPADs. The first enzyme may be omitted from the negative test regions, so that they are not sensitive to the biomarker. An example of a chemiluminescence measurement for detecting urate in a sample is described in [4], where uricase is used as the first enzyme.

As a further example, the detection apparatus 100 may be used to perform chemical measurements on a biological sample, e.g. by detecting a pH of the sample. For such a measurement, the sensor elements 104 may be in the form of ISFETs. The ISFETs may then detect changes in pH of the sample following its introduction into the channels 112a-h, as a result of the reactions that occur in the channels. For example the set of reagents may include an enzyme that is arranged to produce ions (e.g. $H^+$) when it reacts with the biomarker. An example of a pH measurement using an ISFET for detecting urea in a sample is described in [4], where urease is used as the enzyme that produces ions in the presence of urea. As another example, glucose may be detected in a sample via an ISFET, using hexokinase as an enzyme which acts on glucose to produce hydrogen ions (see e.g. [5]).

Figure 2:
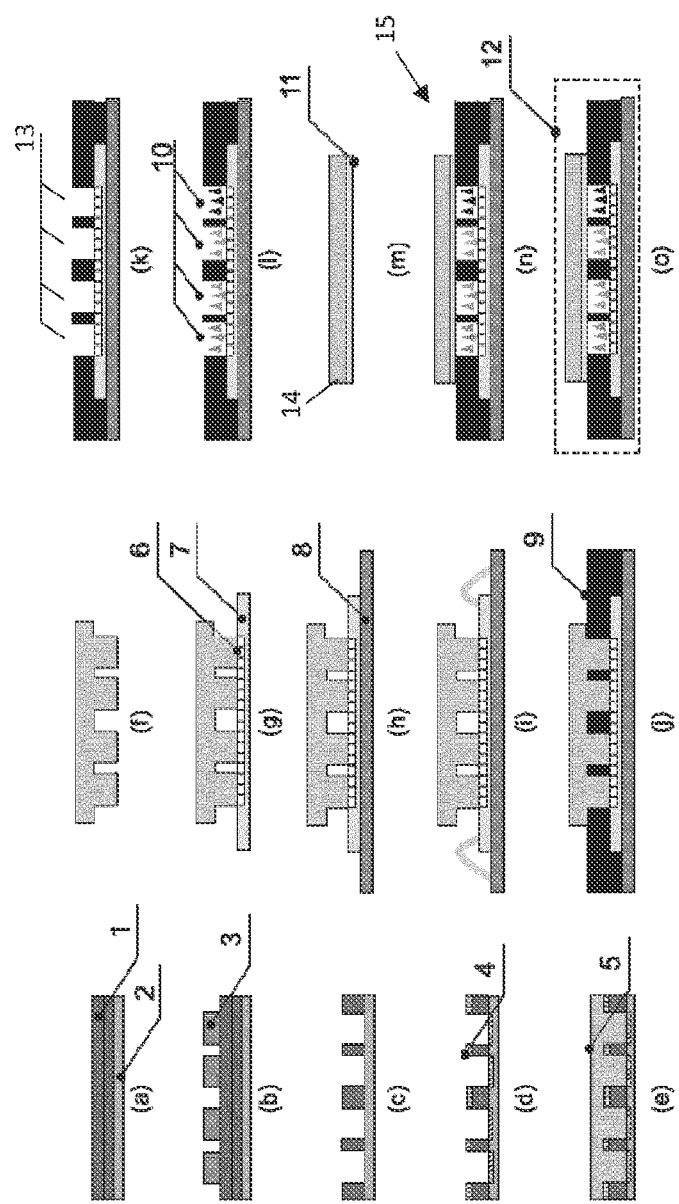
FIG. 2 is a diagram illustrating a series of steps that may be performed to manufacture a detection apparatus, which may be used as part of a system according to an embodiment of the invention.

FIG. 2 illustrates a series of fabrication steps that may be performed to produce a detection apparatus that may be used as part of a system of the invention. For example, the fabrication steps of FIG. 2 may be used to produce the detection apparatus 100 discussed above. The series of steps involves first producing a mould via a photolithography process, the mould being subsequently used to produce a first microstructure. The first microstructure is used to form a second microstructure on a CMOS-based sensor unit via injection moulding. Subsequently, reagents and biomarker samples may be placed in the second microstructure (e.g. in microfluidic channels of the second microstructure), following which the microstructure may be closed to enclose the reagents and biomarker samples therein.

At step (a) shown in FIG. 2, a layer of photoresist 1 (e.g. SU-8) is coated onto a silicon wafer 2, e.g. via spin-coting. More specifically, the silicon wafer may be cleaned with standard procedures, dehydrated for 10 min at 90° C. and plasma-oxidised for 2 min at 120 W. Then SU-8 3050 may be spin-coated on the wafer for 30 s at 1000 rpm and sequentially baked for 1 minute at 65° C., 90 min at 90° C. and 1 min at 65° C. To increase thickness of the microfluidic channels in the microstructure, a second SU-8 3050 layer may be spin-coated and baked with the same recipe on the top of the first SU-8 layer. At step (b), a photomask corresponding to a layout (or arrangement) of the microstructure is arranged over the photoresist. In particular, the photomask may serve to define a reaction zone having a series of microfluidic channels arranged therein. The photoresist is then exposed. For example, the photoresist may be exposed to ultra-violet light using a photolithography mask aligner and then sequentially baked (e.g. for 2 minutes at 65° C., 10 minutes at 90° C. and 2 minutes at 65° C.). At step (c), the photoresist is developed, thus removing portions of the photoresist which were covered by the photomask and thus not exposed. For example, the photoresist may be developed in ethylene carbonate (EC) solvent and then rinsed. The resulting structure provides a mould for forming a first microstructure. At step (d), the mould is silanized, as indicated by reference numeral 4. This may be achieved by exposing the mould to about 30 minutes to Trichloro (1H, 1H,2H,2H-perfluorooctyl)silane in a vacuum chamber. The silanization process may facilitate the subsequent process of removing the first microstructure from the mould.

At step (e), a first microstructure 5 is formed in the mould. For example, the microstructure may be made of Polydimethylsiloxane (PDMS). This may be achieved by pouring a mixture of PDMS and curing agent (e.g. 1:14 ratio) onto the mould. The mixture may be degassed for about one hour in a vacuum chamber to remove air bubbles. The PDMS may be cured by baking the assembly for about two hours at about 70° C. At step (f), after curing the PDMS, the first microstructure may be removed from the mould.

At step (g), the first microstructure is placed onto a CMOS-based sensor unit 7. The sensor unit includes an array of sensor elements 6, and may be similar in configuration to sensor unit 102 discussed above. The first microstructure is aligned over the sensor unit in relation to the array of sensor elements, to ensure that the microfluidic channels will be positioned over desired sensor elements. The first microstructure may be temporarily bonded to the sensor unit using a flip-chip bonder. The first microstructure may be larger than the array of sensor elements, but should not cover any bonding pads of the sensor unit.

At step (h), the sensor unit is bonded to a substrate 8 in the form of a ceramic chip carrier. The sensor unit may be bonded to the chip carrier using an epoxy resin. At step (i), bonding pads on the CMOS-based sensor unit are wire-bonded to the chip carrier. The bonding pads may serve a similar function to the bonding pads 105 discussed above. At step (j), injection moulding is performed to form a second microstructure 9 on the surface of the sensor unit. The second microstructure may be formed by flowing a mixture of epoxy resin and curing agent into the first microstructure. The epoxy resin of the second microstructure also covers the wire bonds from the sensor unit to the chip carrier.

After curing the epoxy (e.g. for about 48 hours at room temperature), the first microstructure may be removed at step (k), thus leaving the second microstructure on the sensor unit and chip carrier. The second microstructure defines a series of microfluidic channels 13 arranged over the array of sensor elements on the sensor unit. In the example shown, the second microstructure includes four channels, however the process of FIG. 2 may be modified to provide any number and configuration of channels (e.g. by adapting the photomask 3 accordingly). For example, the second microstructure may be provided with eight channels, as is the case for detection apparatus 100.

At step (l), reagents and biomarker samples are loaded into the microfluidic channels as appropriate. Similarly to the discussion in relation to FIG. 1, the microfluidic channels may define a test region, first positive control region, second positive control region and a negative control region. A set of reagents including a reagent that is specific to the biomarker of interest is loaded into channels corresponding to the test region, first positive control region, and second positive control region. The same set of reagents is loaded into the channel(s) corresponding to the negative control region, except that the reagent that is specific to the biomarker is omitted from the negative control region. The first and second positive control regions are further loaded with samples of the biomarker. The reagents and biomarker samples may be loaded into the channels using any suitable technique, such as one or more of immobilisation, entrapment, encapsulation, and printing. The reagents and biomarker samples may then be freeze-dried or otherwise dehydrated, in order to remove moisture therefrom.

At step (m), a PDMS slab 14 is fabricated, and provided with a polyvinyl alcohol (PVA) coating 11 on its underside. At step (n), the detection apparatus 15 is finalised by bonding the PDMS slab to the second microstructure, such that the PDMS slab forms a lid covering the microfluidic channels. In this manner, the reagents and biomarker samples are enclosed within the channels. The PVA coating on the PDMS slab provides a biocompatible coating that faces the microfluidic channels. At step (o), the detection apparatus is vacuum-sealed inside packaging 12. This may serve to preserve the reagents and samples of biomarker contained in the channels, e.g. by preventing exposure to atmosphere. The packaging may then be opened when the detection apparatus is to be used for a measurement.

It should be noted that techniques other than that shown in FIG. 2 may be used for providing a microstructure of the surface of the sensor unit. For example, other suitable techniques include hot embossing, soft lithography, and printing techniques.

Figure 3:
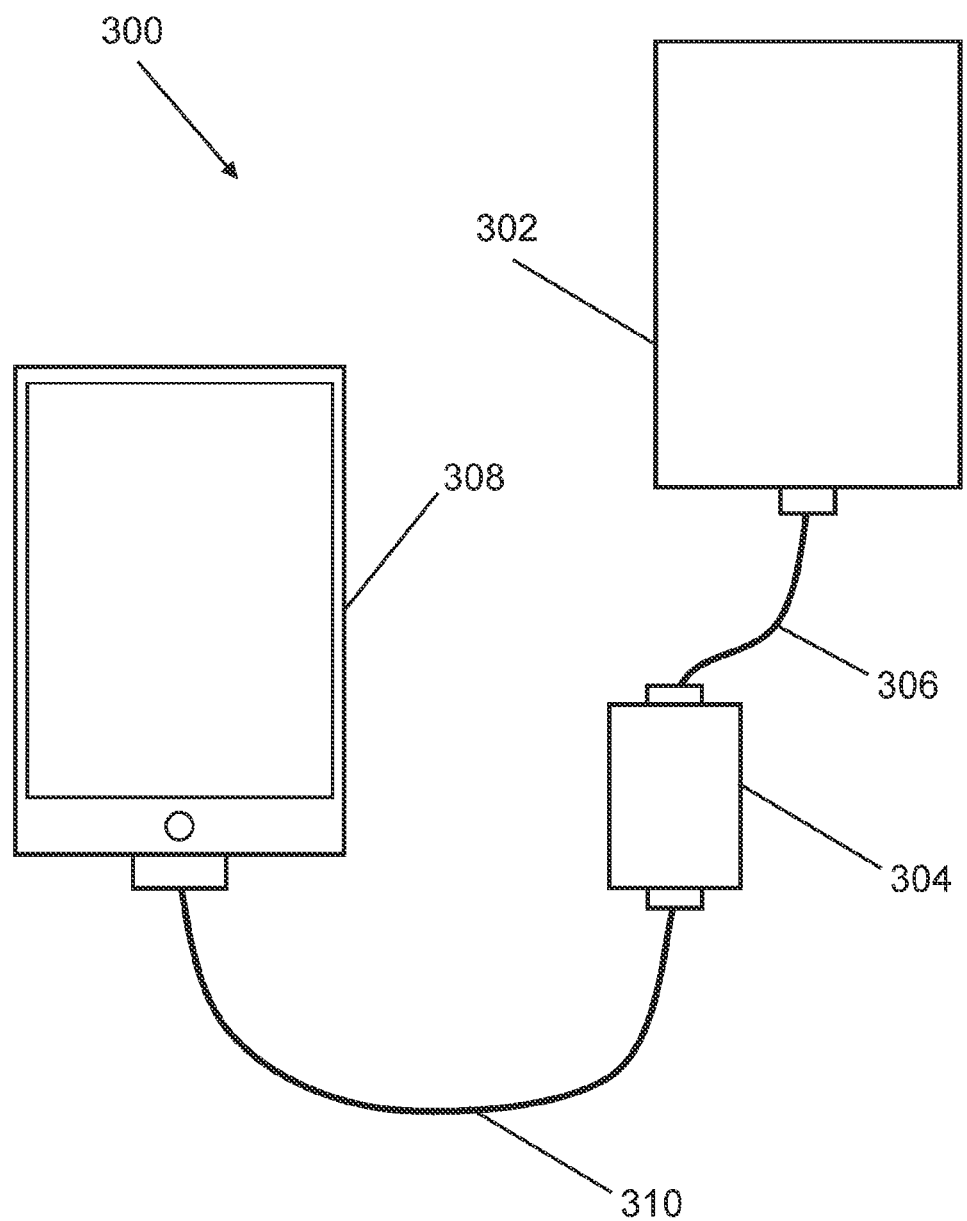
FIG. 3 is a schematic diagram of a system according to an embodiment of the invention for detecting a biomarker in a biological sample.

FIG. 3 shows a schematic diagram of a system 300 according to an embodiment of the invention. The system 300 includes a detection apparatus 302 for detecting a biomarker in a biological sample, and a controller in the form of a reader device 304. The detection apparatus 302 may, for example, correspond to the detection apparatus 100 described above. In particular, the detection apparatus 302 includes a sample receiving module for receiving a biological sample, a reaction zone having a test region, positive control region and negative control region, and a CMOS-based sensor unit for detecting properties of the regions in the reaction zone.

The reader device 304 is communicatively coupled to the detection apparatus 302 so that signals may be exchanged between the reader device 304 and the detection apparatus 302. In the example shown, the reader device 304 is connected to the detection apparatus via a cable 306. For example, the cable 306 may be a USB cable. The cable 306 is connected between a connector on the detection apparatus 302 and a corresponding connector on the reader device 304. The connector on the detection apparatus 302 is electrically coupled to the sensor unit (e.g. via a PCB in the apparatus 302), so that output signals from the sensor unit can be provided to the reader device 304. Although cable 306 is used in the example of FIG. 3, in some examples, there may be no need for a cable between the reader device 304 and the detection apparatus 302. For example, the reader device 304 may be configured to be plugged directly into the detection apparatus 302. As another example, the reader 304 may include a connection slot that is configured to receive a connector on the detection apparatus 302. In some cases, the reader device 304 may be in communication with the detection apparatus 302 via a wireless connection.

The reader device 304 is configured to control measurements performed by the sensor unit in the detection apparatus 302, and to receive output signals from the detection apparatus 302 that are indicative of measurement results from the sensor unit. So, for example, the reader device 304 may receive output signals from the detection apparatus 302 corresponding to individual sensor elements of the sensor unit. The reader device 304 is further configured to determine information related to a presence of the biomarker in the biological sample, as discussed below. The reader device 304 may include a processor for performing the required control and data processing steps, as well as an internal memory for storing data. The processor may implement one or more algorithms that are used for controlling the sensor unit and for processing the output signals from the sensor unit.

The detection apparatus 302 may be provided as a cartridge or similar, which is configured for single use. Thus, the detection apparatus 302 may be disposed of or recycled, after it is used for a measurement on a biological sample. By providing the reader device 304 separately from the detection apparatus 302, the reader device 304 may be disconnected from the detection apparatus 302 after a measurement is completed, so that the detection apparatus 302 can be appropriately disposed of. In this manner, the reader device 304 may be re-used with another detection apparatus. That said, in other cases, the reader device 304 may be integrated with the detection apparatus 302, i.e. the reader device 304 and detection apparatus may be provided as a single device.

We will now describe an example of steps that may be performed by the reader device 304 in order to detect a biomarker in a biological sample, where the detection apparatus 302 corresponds to the detection apparatus 100 described above. The reader device 304 may communicate with the detection apparatus 100, in order to receive output signals corresponding to each sensor element 104 in the sensor unit 102.

To begin a measurement, a biological sample is introduced into the sample receiving area 114 of the detection apparatus, following which the biological sample is distributed amongst the microfluidic channels 112a-h. As the biological sample flows along the microfluidic channels 112a-h, reactions may be initiated with the reagents contained in the channels. In this manner, reactions occurring simultaneously in the different channels may be detected using the sensor unit 102. The reader device 304 may be configured to detect a beginning of the reaction in each channel, by monitoring the output signals of the sensor elements 104 in each channel. For example, the reader device 304 may apply a peak detection (or peak-picking) algorithm to the output signal for each sensor element. In this manner, a peak in the rate of change of the output signal for each sensor element may be detected, which may be indicative of the beginning of a reaction at that sensor element.

The reader device 304 may also be configured to determine whether any of the channels is under-filled, e.g. if there is not enough biological sample to fill each channel. Under-filling of a channel may be detected, for example, where the output signals for one or more sensor elements in the channel do not change following introduction of the biological sample to the apparatus. Where such an under-filling is detected, the reader device 304 may produce a warning, and prompt the user to place more biological sample in the sample receiving area 114.

The reader device 304 may be configured to average together the output signals for each sensor element in a given region of the reaction zone, thus producing a respective averaged signal for each region. Thus, the reader device 304 may produce an average test region signal based on the output signals for the sensor elements in the channels 112d, 112e. Similarly, the reader device 304 may produce an average negative control region signal based on the output signals for the sensor elements in the channels 112a, 112h which correspond to the negative control regions. A first average positive control signal may be produced based on the output signals for the sensor elements in the channels 112c and 112f, and a second average positive control signal may be produced based on the output signals for the sensor elements in the channels 112b and 112g. Averaging the output signals across the sensor elements in this manner may minimise effects due to variations along the lengths of the channels, as well as effects due to variations between channels.

Prior to performing the averaging of the output signals mentioned above, the reader device 304 may apply any suitable form of filtering to the output signals, e.g. such as applying a low-pass filter to the output signals. The reader device 304 may also be configured to check the output signal for each sensor element for excessive noise or other artefacts which may be indicative of a defective sensor element. If a sensor element is found to be defective, the output signal for that sensor may be disregarded in the averaging process, such that it is not taken into account. The reader device 304 may also be configured to truncate the output signals that are received from the detection apparatus, e.g. so that only a time window of interest is taken into account in the analysis. For example, the reader device 304 may be configured to truncate the output signals based on a detected start of the reactions in the reaction zone, such that portions of the output signals occurring prior to start of the reactions may be discarded.

After averaging the output signals as discussed above, reader device 304 may be configured to fit the average output signal for each region to a suitable model (e.g. to a polynomial or exponential model), to facilitate analysis of the data. The rate of change of the average output signal for each region following introduction of the biological sample may be indicative of an initial reaction rate in that region. Accordingly, the reader device 304 subsequently determines a value related to an initial reaction rate for each region in the reaction zone, based on the rate of change of the average output signal for each region. For example, the reader device 304 may determine values $r_t$, $r_n$, $r_a$ and $r_b$ by differentiating the fitted average output signals for the test region, negative control region, first positive control region, and second positive control region, respectively. Thus, values $r_t$, $r_n$, $r_a$ and $r_b$ may be indicative of initial reaction rates in the test region, negative control region, first positive control region, and second positive control region, respectively.

The reader device 304 may be configured to confirm integrity (or validity) or the output signals received from the detection apparatus by verifying the condition $r_n<r_t<r_a<r_b$. Indeed, as noted above, the negative control region is not sensitive to the biomarker, so the reaction rate in the negative control region should be below that of the test region. The positive control regions are both provided with a sample of biomarker, resulting in a higher concentration of biomarker in the positive control regions compared to the test region. This should result in a higher reaction rate in the positive control regions compared to the test region. Additionally, the biomarker sample in the second positive control region has a greater concentration than the biomarker sample in the first positive control region, such that the reaction rate in the second positive control region should be greater than in the first positive control region.

Using the obtained values, the reader device 304 may calculate an adjusted rate $r_t^*=r_t-r_n$ for the test region. The adjusted rate $r_t^*$ for the test region has removed therefrom activity which is not due to presence of the biomarker in the biological sample, as indicated by the reading from the negative control region. The reader device 304 may further calculate a sensitivity S of the sensor unit to presence of the biomarker in the biological sample. The sensitivity may be calculated as:

$$S = \frac{r_b - r_a}{B - A}$$

where A corresponds to a concentration of the samples of the biomarker in the first positive control region (i.e. in channels 112c and 112f), and B corresponds to a concentration of the samples of the biomarker in the second positive control region (i.e. in channels 112b and 112g). The reader device 304 may then be configured to determine a concentration T of the biomarker in the biological sample, using the equation:

$$T = \frac{r_t^*}{S}$$

Alternatively, the concentration T may be determined using the Michaelis-Menten model. If needed, the reader device 304 may further adjust the result for the concentration T in order to compensate for various experimental conditions. For example, the reader device 304 may take into account factors such as dilution factor of the biological sample, enzyme kinetics, temperature, humidity, age or storage time of the detection apparatus (including the reagents), in order to compensate for such factors.

Returning to FIG. 3, the reader device 304 may have a display for outputting the determined biomarker concentration. The reader device 304 may also have an input interface (e.g. in the form of one or more buttons), to enable a user to control the reader device 304. The reader device 304 may further be configured to output data to an external computing device. In the example shown in FIG. 3, the reader device 304 is communicatively coupled to a computing device 308 via a cable 310. For example, the cable 310 may be a USB cable. However, in other examples, the reader device 304 may be in communication with the computing device 308 via a wireless connection (e.g. Bluetooth®). The computing device 308 may be any suitable computing device, such as a smartphone, tablet computer, laptop or desktop computer.

The computing device 308 may be configured to receive and store data from the reader device 304. For example, the computing device may receive data corresponding to the biomarker concentration determined by the reader device 304. The computing device 308 may be configured to display, and/or perform further processing on the data received by the reader device 308. The computing device 308 may also be configured to transmit control signals to the reader device 308, e.g. in order to cause the reader device 308 to perform a measurement with the detection apparatus 302. The computing device 308 may also be connected to the internet, and configured to upload the received data to a cloud service, which is configured to further analyse or use the received data.

In some embodiments, the computing device 308, rather than the reader device 304, may be configured to detect the biomarker and/or determine biomarker concentration. In such an embodiment, the reader device 304 may be configured to sequentially address the sensor elements (e.g. sensor elements 104) in the detection apparatus 302 to obtain detection signals therefrom. The reader device 304 may then digitize the detection signals and transmit them to the computing device 308 for processing. Thus, the computing device 308 may store and process the signals received from the reader device 304 in order to detect presence of the biomarker and/or determine biomarker concentration. The computing device 308 may perform any of the steps discussed above in relation to the reader device 304 for processing the signals. The computing device 308 may have suitable software installed thereon for performing the required processing steps.

In some embodiments, the computing device 308 may be configured to implement a model and/or algorithm for classifying the biological sample measured in the detection apparatus 302 based on the detection/quantification of the biomarker in the sample. For example, the computing device 308 may include a classification model for classifying the sample as "healthy" or "non-healthy", based on the detection/quantification result received from the reader device 304.

Although in the example shown the reader device 304 and computing device 308 are provided as separate devices, in some cases they may be implemented by a single device that is connected to the detection apparatus 302. For example, in some embodiments, the computing device 308 may have software installed thereon for controlling measurements performed by the detection apparatus. Then, the computing device 308 may be connected directly to the detection apparatus without need for a separate reader device, i.e. the computing device 308 may act as a controller of the system 300.

The reader device 304 and/or computing device may use any suitable methods for processing and analysing data obtained from the detection apparatus 302. By way of example, methods used for processing and analysing data obtained from the detection apparatus 302 may include:

methods for noise reduction, such as averaging, filtering, Fourier transforms, wavelet transforms, z-transforms, block-matching algorithm, noise cancellation algorithms, outlier detection, peak-peaking, Kalman filtering and any other suitable method;

methods for data handling such as conversion, data mining, compression, prediction, coding and any other suitable means;

methods for normalisation and standardisation, such as centering, auto-scaling, range scaling, vast scaling, level scaling, Pareto-scaling, log transform, power transform, standard score, student's t-statistics, studentized statistic, standardised moment, coefficient of variation, min-max feature scaling, variance-to-mean scaling, normal score, quantile normalisation and any other suitable method;

methods for extracting statistical quantities, such as probability density function, minimum, maximum, average, median, standard deviation, variance, skewness, range, quartile and any other suitable method and quantity;

methods for univariate analysis, such as covariance matrix, correlation matrix, t-test, volcano plot, frequency distribution tables, bar charts, histograms, frequency polygons, statistical description, scoring, ranking and any other suitable methods;

methods for multivariate analysis, such as ANOVA, MANOVA, Wilk's test, Roy's test, Kruskal-Wallis, regressions, contrasts, profile analysis, growth curves, discriminant analysis, factor analysis and any other suitable technique;

methods for producing a Receiver Operating Characteristic (ROC) curve;

methods for clustering and ordination such as partitioning, fuzzy clustering, density-based clustering, partial least square regression (PLS), principal component analysis (PCA), independent component analysis (ICA), polar ordination, correspondence analysis, direct gradient analysis (DCA), canonical correspondence analysis (CCA), singular value decomposition (SVD), loading, scores, redundancy analysis, principal coordinates analysis (PCoA), chi-squared metric and any other suitable method;

methods for classification, such as dimensionality reduction, decision trees, discriminant analysis, regression analysis, support vector machines (SVM), nearest neighbour classifier, ensemble classifier, Bayesian networks, and any other suitable methods;

methods for machine learning, such as feature extraction, supervised/unsupervised learning, deep learning, self-learning, feature learning, anomaly detection, association rules, neural networks, transfer learning, reinforcement learning, natural language processing, word embedding, hidden layer, learning vector quantization (LVQ), locally weighted learning (LWL), ridge regression, least-angle regression (LARS), elastic net, least absolute shrinkage and selection operator (LASSO), self-organizing map (SOM), iterative dichotomiser 3 (ID3), C4.5, C5.0, chi-squared automatic interaction detection (CHAID), decision stump, M5, conditional decision trees, apriori algorithm, eclat algorithm, Hopfield Network and any other suitable method.

We now describe an example application of the invention, involving the early diagnosis of prostate cancer (PCa). PCa has the highest cancer incidences for males (26%) in the UK. It is well established that the early diagnosis of the disease can have a dramatic impact on prognosis. Metabolomics can potentially provide a means for early diagnosis of PCa. Cancer cells produce substantial and detectable modifications in human metabolism, and cancer-related metabolites accumulate as a consequence of genetic changes. Thus, altered levels of metabolites can act as signalling molecules to detect/monitor several types of cancer. There is strong evidence that increased level of L-type amino acids (LAA), glutamate and choline in human blood can help to predict and diagnose PCa.

The inventors performed a series of experiments with a system according to the invention, to demonstrate colorimetric quantification of the above-mentioned PCa-related metabolites. Biological samples tested included human plasma from ten healthy subjects and sixteen subjects affected by PCa. Non-cancer samples were purchased by Cambridge Bioscience to be used as a control group. Donors were selected to be adult male subjects only. The average age of the non-PCa group was 34±10 years. The ethnicity of the group was diversified including European, Asian and African donors. Samples were tested for the most common infective diseases, including HIV, syphilis, HCV, HBsAg and all resulted negative. Approximately 10 mL of fresh blood samples were collected in various research centres in England, mixed with 10 mg of K2EDTA anticoagulant, centrifuged and the resulting 4 ml of plasma samples were frozen at −80° C. Frozen plasma samples were shipped under dry-ice. After collection, plasma samples were aliquoted in 200 µL vials and stored in at −80° C. No additional freeze and taw cycle was performed. PCa samples were sourced by the Beatson Cancer Institute (Glasgow, UK) under ethical approval. Donors were selected to be adults already diagnosed with PCa. General knowledge of the drug treatment of the patients was available. All samples were under similar standard therapy, including triptorelin (or similar), omeprazole/esomeprazole, and statins. Approximately 10 mL of blood samples were collected at the Beatson Cancer Institute, mixed with 10 mg of K2EDTA anticoagulant, centrifuged and the resulting plasma samples were frozen at −80° C. Samples were collected from the Beatson Cancer Institute and transported in dry-ice. Afterwards, plasma samples were aliquoted in 200 µL vials and stored at −80° freezer. No additional freeze and thaw cycle was performed. Samples were stored and tested in the same facilities as the non-PCa group.

The system used for the experiments involved a detection apparatus similar to that described in relation to FIG. 1, where the CMOS-based sensor unit included a 16×16 array of photodiodes for performing colorimetric measurements. In the system used, four microfluidic channels were defined on the CMOS-based sensor unit. For these proof of principle experiments, reagents were mixed with the sample off-chip and introduced into the reaction zone after a few seconds. This allowed the same channels to be used to perform each of the measurements set out below in sequence. However, as discussed above with respect to FIG. 1 in embodiments of the invention, each type of measurement may have one or more dedicated channels that have the reagents (where required) already in place, so that no off-chip pre-treatment of the sample is required.

The three metabolites (LAA, glutamate and choline) were tested separately. For each metabolite, a negative control measurement was performed, followed by a colorimetric measurement performed in triplicate (herein referred to as biological replicates), and finally two positive control measurements. As four microfluidic channels were used, each measurement yielded four separate results, herein referred to as technical replicates. Technical replicates with unexpected behaviour (e.g. outliers) or affected by noise (e.g. due to an air bubble or fluidic failure) were excluded. Data from technical replicates were averaged. Thus, for each biological replicate, one result was obtained. The result for each concentration was obtained as the average and standard deviation over the biological replicates.

As discussed above, the negative control measurement served to quantify a colour change which is not related to the reaction with the metabolite under test (i.e. non-specific activity). The positive control measurements are designed to create a detectable signal whatever the properties of the sample. For the first positive control measurement an additional concentration A of the metabolite under test was added to the sample, and for the second positive control measurement, an additional concentration B=2A of the metabolite under test was added to the sample. The additional concentration A for the positive controls was A=500 µM for LAA, A=100 µM for glutamate, and A=100 µM for choline. Details of assay formulations used for the measurements are provided below in Table 1. The CMOS-based sensor unit was cleaned between measurements to avoid cross-contamination.

TABLE 1

Assay formulations

| | LAA | Glutamate | Choline |
|---|---|---|---|
| Sensor unit | 4 parallel and identical microchannels on CMOS-based sensor unit | | |
| Microchannel dimensions | width = 300 µm; height = 270 µm; length = 4 mm → Volume: 0.324 µL | | |
| Light source | LED @ 490 nm (3 mW, FWHM = 20 nm) | | |
| Total Volume | 40 µL | | |
| Sample Volume | 20 µL | | |
| Reagent mix volume | 20 µL | | |
| Reagent buffer | DI water | | |
| $1^{st}$ reaction stage | LAAOx (6.7 µL, 10 U/mL) | GlOx (6.7 µL, 4 U/mL) | ChOx (6.7 µL, 150 U/mL) |
| $2^{nd}$ reaction stage | 6.7 µL HRP 300 U/ml 3.3 µL Phenol 44.5 mM 3.3 µL 4-AAP 10.5 mM | | |
| Negative control | $1^{st}$ reaction stage is substituted with 10 µL of DI water | | |
| Positive control | The sample is spiked with a known concentration of the metabolite of interest | | |

Table 1 provides details of the setup used for performing the measurements, including dimensions of the microfluidic channels and an indication of the light source used for performing the colorimetric measurements. The "$1^{st}$ reaction stage" row indicates reagents used in the reagent mix for each metabolite, which are specific to the metabolite under test. The specific reagents are enzymes LAA-oxidase, glutamate oxidase and choline oxidase for LAA, glutamate and choline, respectively. The "$2^{nd}$ reaction stage" row indicates reagents which are used to produce a change in colour of the sample following the reaction of the metabolite under test with the reagent in the $1^{st}$ reaction stage. The reagents for the $2^{nd}$ reaction stage are horseradish peroxidase (HRP), phenol and 4-antipyrine (4-AAP). As indicated in Table 1, the reagents for the $1^{st}$ reaction stage are omitted from the negative controls. The metabolites were detected and quantified in the samples using the set of equations described above in relation to the reader device 304.

Calibration measurements were performed to demonstrate suitability of the system for quantifying the target metabolites in their physiological range. A summary of the calibration results is provided in Table 2, below.

TABLE 2

Calibration Results

| | LAA | Glutamate | Choline |
|---|---|---|---|
| Test Range | 0-5 mM | 0-1.5 mM | 0-0.6 µM |
| Physiological range | 1-4 mM | 20-150 µM | 10-40 µM |
| Relation with PCa | ↑ | ↑ | ↑ |
| microfluidic channel size (w × h) | 330 µm × 290 µm | | |
| $K_m$ (µM) | 3906 | 863.1 | 1141 |
| $V_m$ (mV/s) | 3.93 | 5.58 | 9.45 |
| offset (mV/s) | −0.05 | 0.03 | 0.05 |
| Model | $y = (V_m * x)/(K_m + x) + c$ | | |
| Model goodness | $R^2 > 0.99$ | $R^2 > 0.97$ | $R^2 > 0.97$ |
| LOD (µM) | 14 | 2.2 | 1.7 |
| LOQ (µM) | 32 | 5 | 3.9 |

The calibration measurements were performed with spiked human plasma (i.e. human plasma where a quantity of the biomarker was artificially added). The "Test Range" row of Table 2 indicates a range of concentrations of the metabolites that were used for the calibration measurements, whilst the "Physiological range" row indicates the range of concentrations typically found for the metabolites in human serum. The arrows "Relation with PCa" row indicate that there is known to be increased levels of these metabolites in patients that are known to be affected by PCa (see e.g. references [6-15]). Kinetics parameters of the reactions in the microfluidic channels were estimated using the Michaelis-Menten model (shown in the "Model" row of Table 2). In particular, the Michaelis constant $K_m$, the initial reaction rate $V_m$, and the offset c were estimated for the Michaelis-Menten model. The "Model goodness" row in Table 2 indicates the coefficient of determination ($R^2$) value for the fit to the model, which provides an indication of how well the model fits the data. The limit of detection (LOD) and limit of quantification (LOQ) were also estimated, according to the International Union of Pure and Applied Chemistry (IUPAC) definition. The results of Table 2 clearly indicate that the system of the invention is capable of detecting and quantifying LAA, glutamate and choline in biological sample, within typical physiological ranges.

Results of measurements performed on the ten healthy samples and the sixteen PCa samples are summarised in Table 3 below.

TABLE 3

Measurement results

| Normalized to: | Group | LAA 2.4 mM | Glutamate 53.7 µM | Choline 9.2 µM |
|---|---|---|---|---|
| 1 | non-PCa | 0.79 | 0.79 | 0.21 |
| 2 | non-PCa | 1.03 | 1.25 | 0.57 |
| 3 | non-PCa | 0.82 | 0.57 | 0.21 |
| 4 | non-PCa | 1.31 | 0.64 | 0.69 |
| 5 | non-PCa | 0.82 | 0.74 | 1.46 |
| 6 | non-PCa | 0.90 | 0.88 | 0.63 |
| 7 | non-PCa | 0.74 | 0.70 | 0.63 |
| 8 | non-PCa | 0.50 | 0.41 | 0.73 |
| 9 | non-PCa | 0.57 | 0.76 | 0.97 |
| 10 | non-PCa | 0.70 | 0.75 | 0.21 |
| 11 | PCa | 0.72 | 1.41 | 0.45 |
| 12 | PCa | 1.17 | 0.12 | 1.61 |
| 13 | PCa | 1.72 | 1.15 | 0.59 |
| 14 | PCa | 2.24 | 1.16 | 0.81 |
| 15 | PCa | 1.70 | 0.91 | 1.56 |

TABLE 3-continued

Measurement results

| Normalized to: | Group | LAA 2.4 mM | Glutamate 53.7 μM | Choline 9.2 μM |
|---|---|---|---|---|
| 16 | PCa | 1.44 | 2.78 | 0.21 |
| 17 | PCa | 1.19 | 0.62 | 1.64 |
| 18 | PCa | 1.04 | 0.63 | 1.29 |
| 19 | PCa | 0.77 | 1.12 | 0.43 |
| 20 | PCa | 1.02 | 0.86 | 2.25 |
| 21 | PCa | 0.80 | 1.57 | 3.52 |
| 22 | PCa | 0.74 | 1.37 | 0.70 |
| 23 | PCa | 0.95 | 1.11 | 1.69 |
| 24 | PCa | 0.62 | 1.40 | 0.97 |
| 25 | PCa | 0.80 | 1.27 | 0.72 |
| 26 | PCa | 0.89 | 1.04 | 0.49 |

TABLE 4

Summary of results

| Average non-PCa | 0.8 | 0.7 | 0.6 |
|---|---|---|---|
| Average PCa | 1.1 | 1.2 | 1.2 |
| t-test (p) | 0.034 | 0.02 | 0.034 |

The rows labelled 1-26 in Table 3 indicate the different samples measured, whilst the "Group" column indicates whether the corresponding sample corresponds to a healthy sample or a sample with PCa. The LAA, glutamate and choline columns indicate the normalised concentration values determined for each sample. The normalised concentration values reported in Table 3 were averaged over three separate measurements. The concentration values for each metabolite are normalised relative to an average concentration of that metabolite over all samples (including both PCa and non-PCa samples), as indicated in the "Normalised to" row of Table 3.

Figure 4:
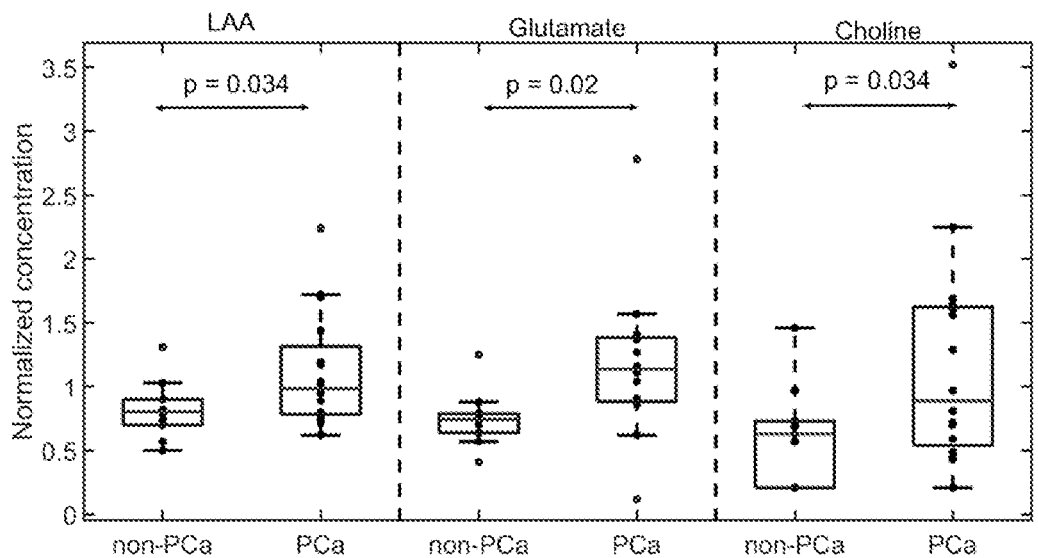
FIG. 4 is a graph showing normalised concentrations of metabolites measured in samples of blood serum, using a system according to an embodiment of the invention.

Table 4 above shows averages of the normalised concentrations for the non-PCa and PCa samples. As can be seen, PCa samples have an increased concentration of LAA, glutamate and choline compared to non-PCa samples. Thus, the detection and quantification of any one of these metabolites with the system of the invention may enable a sample to be classified as being healthy or indicative of PCa. The last row of Table 4 indicates the p-value determined for each metabolite. FIG. 4 shows plots of the measured normalised concentrations for each of the three metabolites.

Many different classification techniques and models can be used in order to classify a sample as PCa or non-PCa, based on the measured concentrations of the metabolites for that sample. Such a classification technique or model may, for example, be implemented by the computing device 308 of system 300 discussed above. As an example, the inventors used a linear scoring model that was optimised by Monte-Carlo simulation, in order to classify samples. For each sample, the linear score was calculated using the following equation:

$$\text{Score} = \text{LAA} \cdot W1 + \text{glutamate} \cdot W2 + \text{choline} \cdot W3 \quad (5)$$

"LAA", "glutamate" and "choline" in the above equation correspond to the normalised concentrations measured for those metabolites in the sample. W1, W2 and W3 correspond to coefficients of the model that were optimised by the Monte-Carlo simulation. A threshold classifier (determined by the simulation) was then used to classify a sample as a PCa or non-PCa sample, based on whether the calculated score for a sample was above or below the threshold. The model correctly classified 90% and 81.5% of measured non-PCa and PCa samples, respectively. 10% of non-PCa samples were wrongly classified as PCa (false positive). Similarly, 18.5% of PCa samples were wrongly classified as non-PCa (false negative).

Figure 5:
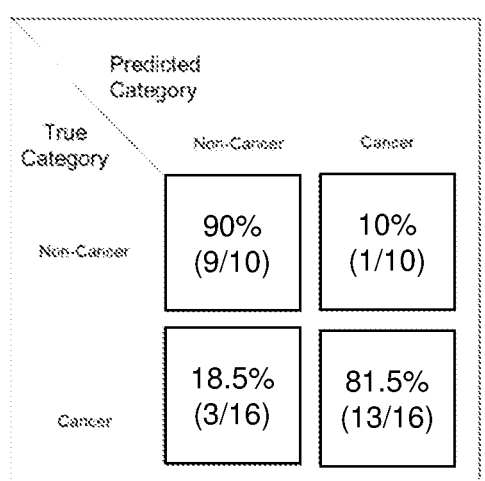
FIG. 5(a) shows a confusion matrix of a linear scoring model used to classify samples based on metabolite concentration measurements obtained using a system according to an embodiment of the invention.
FIG. 5(b) is a graph showing scores calculated with the linear scoring model for the blood serum samples of FIG. 4.
Figure 5:
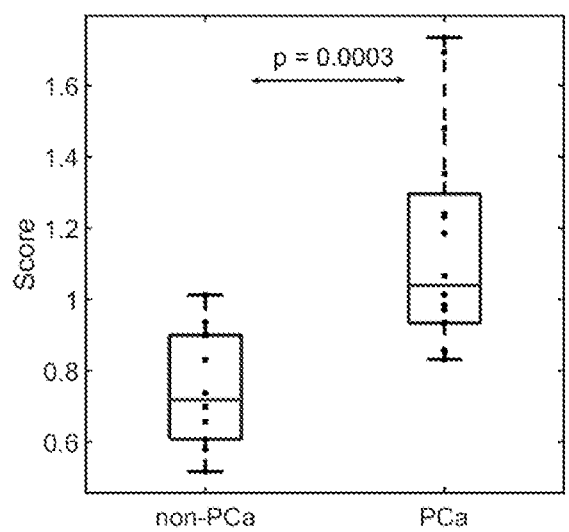

FIG. 5 illustrates results of the linear scoring model used to classify samples. Panel (a) of FIG. 5 shows a "confusion matrix", which illustrates a performance of the model in terms of predicting whether a sample is PCa or non-PCa. Panel (a) of FIG. 5 also indicates the values of W1, W2 and W3 and of the threshold classifier used in the model. Panel (b) of FIG. 5 shows a plot of the scores calculated for each of the PCa and non-PCa samples of Table 2 using equation (5), as well as an indication of the p-value for the model. Receiver operating characteristic (ROC) curves can also be created, to illustrate a diagnostic ability of the model.

Other statistical and/or computational techniques may be used for classifying samples based on the measured metabolite concentrations. As an example, a machine learning model may be trained to classify samples as PCa or non-PCa based on the metabolite concentrations for those samples.

The invention claimed is:

1. A detection apparatus for detecting a biomarker in a biological sample, the detection apparatus comprising:
 a sample receiving module arranged to receive the biological sample in a reaction zone, the reaction zone comprising:
  a test region that is sensitive to presence of the biomarker in the biological sample;
  a positive control region that is sensitive to presence of the biomarker in the biological sample, and which includes a pre-loaded portion of the biomarker; and
  a negative control region that is not sensitive to presence of the biomarker in the biological sample; and
 a CMOS-based sensor unit configured to:
  independently detect a property of each of the test region, the positive control region, and the negative control region, and
  output a respective detection signal for each of the test region, the positive control region, and the negative control region,
 wherein the CMOS-based sensor unit is communicable with an analysis module that is configured to determine information related to a presence of the biomarker in the biological sample using the respective detection signals from the test region, the positive control region, and the negative control region.

2. The detection apparatus of claim 1, wherein the sample receiving module comprises a sample receiving area and a transport structure configured to convey the biological sample received at the sample receiving area to the reaction zone.

3. The detection apparatus of claim 2, wherein the transport structure is configured to entrain the pre-loaded portion with the biological sample before it enters the positive control region.

4. The detection apparatus of claim 2, wherein the transport structure comprises one or more microfluidic channels or wells for each of the test region, positive control region and negative control region.

5. The detection apparatus of claim 4, wherein each microfluidic channel or well is defined by a microstructure which is disposed on the CMOS-based sensor unit.

6. The detection apparatus of claim 4, wherein each microfluidic channel or well is covered by a lid.

7. The detection apparatus of claim 1, wherein the CMOS-based sensor unit is configured to simultaneously detect the properties of the test region, positive control region and negative control region.

8. The detection apparatus of claim 1, wherein:
the positive control region includes a first positive control region and a second positive control region, the first positive control region including a first pre-loaded portion of the biomarker and the second control region including a second pre-loaded portion of the biomarker, the second pre-loaded portion including a larger amount of the biomarker than the first preloaded portion; and
the detected property of the positive control region includes independently detected properties of the first positive control region and the second positive control region.

9. The detection apparatus of claim 1, wherein the test region includes a set of reagents configured to cause a change in the detected property of the test region in response to a biological sample comprising the biomarker coming into contact with the test region.

10. The detection apparatus of claim 9, wherein the set of reagents includes a reagent that is specific to the biomarker, and wherein the negative control region includes the set of reagents, except for the reagent that is specific to the biomarker.

11. The detection apparatus of claim 9, wherein the positive control region includes the set of reagents.

12. A system for detecting a biomarker in a biological sample, the system comprising:
a detection apparatus; and
an analysis module,
wherein the detection apparatus comprises:
a sample receiving module arranged to receive the biological sample in a reaction zone, the reaction zone comprising:
a test region that is sensitive to presence of the biomarker in the biological sample;
a positive control region that is sensitive to presence of the biomarker in the biological sample, and which includes a pre-loaded portion of the biomarker; and
a negative control region that is not sensitive to presence of the biomarker in the biological sample; and
a CMOS-based sensor unit configured to:
independently detect a property of each of the test region, the positive control region, and the negative control region, and
output a respective detection signal for each of the test region, the positive control region, and the negative control region,
wherein the CMOS-based sensor unit is communicable with the analysis module, and
wherein the analysis module is configured to determine information related to a presence of the biomarker in the biological sample using the respective detection signals from the test region, the positive control region, and the negative control region.

13. The system of claim 12, wherein the detection apparatus is located in a disposable cartridge, and the analysis module is located in a reader configured to detachably connect to the disposable cartridge.

14. The system of claim 12, wherein the analysis module is configured to:
determine, using the respective detection signals from the test region and the negative control region, information indicative of a reaction rate of a reaction in the test region involving the biomarker,
wherein the information related to a presence of the biomarker is determined in part using the information indicative of a reaction rate.

15. The system of claim 14, wherein the analysis module is further configured to:
determine, using the respective detection signal from the positive control region, information indicative of measurement sensitivity,
wherein the information related to a presence of the biomarker is determined in part using the information indicative of measurement sensitivity.

16. The system of claim 12, wherein the analysis module is further configured to classify the biological sample based on the information related to a presence of the biomarker in the biological sample.

17. A method of detecting a biomarker in a biological sample, the method comprising:
introducing the biological sample into a reaction zone, the reaction zone comprising:
a test region that is sensitive to presence of the biomarker in the biological sample,
a positive control region that is sensitive to presence of the biomarker in the biological sample, and that includes a pre-loaded portion of the biomarker, and
a negative control region that is not sensitive to presence of the biomarker in the biological sample;
independently detecting, using a CMOS-based sensor unit, a property of each of the test region, the positive control region, and the negative control region;
outputting a respective detection signal for each of the test region, the positive control region, and the negative control region; and
determining, using the respective detection signals from the test region, positive control region and negative control region, information related to presence of the biomarker in the biological sample.

18. The method of claim 17, comprising simultaneously detecting the properties of the test region, positive control region and negative control region.

19. The method of claim 17, wherein determining the information related to a presence of the biomarker in the biological sample includes any of:
determining, using the respective detection signals from the test region and the negative control region, information indicative of a reaction rate of a reaction in the test region involving the biomarker; and
determining, using the respective detection signal from the positive control region, information indicative of a measurement sensitivity.

20. The method of claim 17, further comprising classifying the biological sample based on the information related to a presence of the biomarker in the biological sample.

* * * * *